United States Patent
Fenske

(10) Patent No.: US 9,056,033 B2
(45) Date of Patent: Jun. 16, 2015

(54) HIGHLY FLEXIBLE ABSORBENT LAMINATE AND METHOD FOR PRODUCTION THEREOF

(75) Inventor: Wilfried Fenske, Einhausen (DE)

(73) Assignee: Evonik Industries AG, Essen (DE)

(*) Notice: Subject to any disclaimer, the term of this patent is extended or adjusted under 35 U.S.C. 154(b) by 180 days.

(21) Appl. No.: 13/636,471

(22) PCT Filed: Mar. 28, 2011

(86) PCT No.: PCT/DE2011/000338
§ 371 (c)(1),
(2), (4) Date: Sep. 21, 2012

(87) PCT Pub. No.: WO2011/141009
PCT Pub. Date: Nov. 17, 2011

(65) Prior Publication Data
US 2013/0011601 A1    Jan. 10, 2013

(30) Foreign Application Priority Data
Mar. 28, 2010 (DE) .......... 10 2010 013 288

(51) Int. Cl.
*B32B 3/24* (2006.01)
*B32B 3/28* (2006.01)
(Continued)

(52) U.S. Cl.
CPC ....... *A61F 13/5323* (2013.01); *A61F 13/15617* (2013.01); *B32B 3/28* (2013.01); *A61F 2013/53089* (2013.01); *B32B 5/028* (2013.01); *A61F 13/15601* (2013.01); *B32B 7/045* (2013.01); *B32B 38/0032* (2013.01);
(Continued)

(58) Field of Classification Search
CPC ............. A61F 2013/53051; A61F 2013/53062
USPC .................................................. 604/385.16
See application file for complete search history.

(56) References Cited

U.S. PATENT DOCUMENTS 4,227,952 A    10/1980 Sabee
4,525,407 A *  6/1985 Ness ............................. 428/138
(Continued)

FOREIGN PATENT DOCUMENTS

CN    1984772 A    6/2007
CN    101155564 A    4/2008
(Continued)

OTHER PUBLICATIONS

Machine Translation of JP 2007130819 A, May 2007.*
(Continued)

*Primary Examiner* — Jeff Vonch
(74) *Attorney, Agent, or Firm* — Smith Moore Leatherwood LLP; Philip P. McCann; John P. Zimmer

(57) ABSTRACT

Laminates are described herein. A laminate is characterized in that the laminate contains a water-absorbing polymer known as a super-absorbent polymer (SAP) between one or more elastic interplies, wherein the interplies consist of sheetlike lengths of material which are firmly bonded together on the outside surface of individual threads, strands or bands and this laminate is extendable essentially transversely to the production direction and shirred in a relaxed state, and the elastic interplies contain many individual sections or cassettes of superabsorbent and create room for the expansion of the laminate on fluid imbibition perpendicularly to and within the manufacturing plane.

9 Claims, 7 Drawing Sheets

(51) Int. Cl.

| | | |
|---|---|---|
| *B32B 5/04* | (2006.01) | |
| *B32B 5/08* | (2006.01) | |
| *B32B 5/26* | (2006.01) | |
| *B32B 37/12* | (2006.01) | |
| *B32B 38/04* | (2006.01) | |
| *A61F 13/53* | (2006.01) | |
| *A61F 13/534* | (2006.01) | |
| *A61F 13/537* | (2006.01) | |
| *A61F 13/532* | (2006.01) | |
| *A61F 13/15* | (2006.01) | |
| *B32B 7/04* | (2006.01) | |
| *B32B 7/14* | (2006.01) | |
| *A61F 13/49* | (2006.01) | |
| *A61F 13/539* | (2006.01) | |
| *B32B 5/02* | (2006.01) | |
| *B32B 38/00* | (2006.01) | |
| *B32B 3/26* | (2006.01) | |
| *B32B 37/00* | (2006.01) | |

(52) U.S. Cl.
 CPC .... B32B 3/266 (2013.01); A61F 2013/530868 (2013.01); A61F 2013/530875 (2013.01); *B32B 7/14* (2013.01); B32B 38/04 (2013.01); B32B 37/0076 (2013.01); B32B 37/12 (2013.01); A61F 2013/530897 (2013.01); B32B 2307/73 (2013.01); B32B 2307/728 (2013.01); B32B 37/1292 (2013.01); *A61F 13/15593* (2013.01); *A61F 13/15658* (2013.01); *A61F 13/4902* (2013.01); *A61F 13/539* (2013.01); A61F 2013/49022 (2013.01); A61F 2013/49025 (2013.01); A61F 2013/49055 (2013.01); A61F 2013/53051 (2013.01); A61F 2013/530562 (2013.01); A61F 2013/53445 (2013.01); *B32B 5/04* (2013.01); *B32B 5/26* (2013.01)

(56) References Cited

U.S. PATENT DOCUMENTS

| | | | |
|---|---|---|---|
| 4,753,643 A | 6/1988 | Kassai | |
| 4,842,666 A * | 6/1989 | Werenicz | 156/161 |
| 4,886,511 A * | 12/1989 | Korpman | 604/365 |
| 4,892,535 A * | 1/1990 | Bjornberg et al. | 604/380 |
| 4,994,053 A * | 2/1991 | Lang | 604/367 |
| 5,226,992 A | 7/1993 | Morman | |
| 5,275,676 A | 1/1994 | Rooyakkers et al. | |
| 5,336,545 A | 8/1994 | Morman | |
| 5,366,452 A | 11/1994 | Widlund et al. | |
| 5,411,497 A | 5/1995 | Tanzer et al. | |
| 5,425,725 A | 6/1995 | Tanzer et al. | |
| 5,433,715 A | 7/1995 | Tanzer et al. | |
| 5,451,219 A | 9/1995 | Suzuki et al. | |
| 5,505,718 A | 4/1996 | Roe et al. | |
| 5,514,470 A | 5/1996 | Haffner et al. | |
| 5,562,646 A | 10/1996 | Goldman et al. | |
| 5,593,399 A | 1/1997 | Tanzer et al. | |
| 5,601,542 A | 2/1997 | Melius et al. | |
| 5,643,238 A | 7/1997 | Baker | |
| 5,843,059 A | 12/1998 | Niemeyer et al. | |
| 5,938,650 A * | 8/1999 | Baer et al. | 604/368 |
| 5,938,659 A | 8/1999 | Tu et al. | |
| 5,964,743 A | 10/1999 | Abuto et al. | |
| 6,129,717 A | 10/2000 | Fujioka et al. | |
| 6,149,638 A | 11/2000 | Vogt et al. | |
| 6,231,557 B1 | 5/2001 | Krautkramer et al. | |
| 6,258,196 B1 * | 7/2001 | Suzuki et al. | 156/176 |
| 6,362,389 B1 | 3/2002 | McDowall et al. | |
| 6,420,625 B1 | 7/2002 | Jones et al. | |
| 6,429,350 B1 | 8/2002 | Tanzer et al. | |
| 6,436,081 B1 * | 8/2002 | Wada et al. | 604/385.01 |
| 6,570,056 B1 | 5/2003 | Tanzer et al. | |
| 6,582,413 B2 | 6/2003 | Krautkramer et al. | |
| 6,602,234 B2 | 8/2003 | Klemp et al. | |
| 6,610,900 B1 | 8/2003 | Tanzer | |
| 6,682,512 B2 | 1/2004 | Uitenbroek et al. | |
| 6,790,202 B2 | 9/2004 | Klemp et al. | |
| 6,855,223 B2 | 2/2005 | Johnson | |
| 6,972,011 B2 | 12/2005 | Maeda et al. | |
| 7,037,300 B2 | 5/2006 | Kling | |
| 7,175,910 B2 | 2/2007 | Ehrnsperger et al. | |
| 7,247,152 B2 | 7/2007 | Klemp et al. | |
| 7,361,246 B2 | 4/2008 | Chang et al. | |
| 7,744,576 B2 | 6/2010 | Busam et al. | |
| 7,750,203 B2 | 7/2010 | Becker et al. | |
| 2002/0095127 A1 | 7/2002 | Fish et al. | |
| 2002/0102392 A1 | 8/2002 | Fish et al. | |
| 2002/0115969 A1 | 8/2002 | Maeda et al. | |
| 2003/0225382 A1 | 12/2003 | Tombult-Meyer et al. | |
| 2004/0087923 A1 | 5/2004 | Cole | |
| 2004/0127874 A1 * | 7/2004 | Nishizawa et al. | 604/385.01 |
| 2004/0110325 A1 | 12/2004 | Nanni et al. | |
| 2006/0048880 A1 * | 3/2006 | Blessing et al. | 156/60 |
| 2006/0206073 A1 | 9/2006 | Crane et al. | |
| 2008/0156418 A1 | 7/2008 | Fenske | |

FOREIGN PATENT DOCUMENTS

| | | | | |
|---|---|---|---|---|
| DE | 102004026070 A1 | 12/2005 | | |
| EP | 724418 A1 | 8/1996 | | |
| EP | 0803602 A1 | 10/1997 | | |
| JP | 06269475 A * | 9/1994 | | A61F 13/15 |
| JP | 10165432 A * | 6/1998 | | |
| JP | 11099169 A * | 4/1999 | | A61F 13/15 |
| JP | 2002192641 A | 7/2002 | | |
| JP | 2007130819 A * | 5/2007 | | |
| WO | 9511654 A1 | 5/1995 | | |
| WO | 03041627 A2 | 5/2003 | | |
| WO | 2004011046 A1 | 2/2004 | | |
| WO | 2004071363 A1 | 8/2004 | | |
| WO | 2004071539 A2 | 8/2004 | | |
| WO | 2005115754 A1 | 12/2005 | | |

OTHER PUBLICATIONS

Fenske, U.S. Appl. No. 11/569,454, filed Jun. 6, 2007, Non-Final Office Action dated Jan. 21, 2010.
Fenske, U.S. Appl. No. 11/569,454, filed Jun. 6, 2007, Final Office Action dated Jul. 22, 2010.
Fenske, U.S. Appl. No. 13/636,457, filed Sep. 21, 2012.
German language Written Opinion mailed on Jan. 13, 2012 in PCT/DE2011/000338.
German language Written Opinion mailed on Jan. 13, 2012 in PCT/DE2011/000339.
International Search Report mailed on Jan. 13, 2012 in PCT/DE2011/000338.
International Search Report mailed on Jan. 13, 2012 in PCT/DE2011/000339.

* cited by examiner

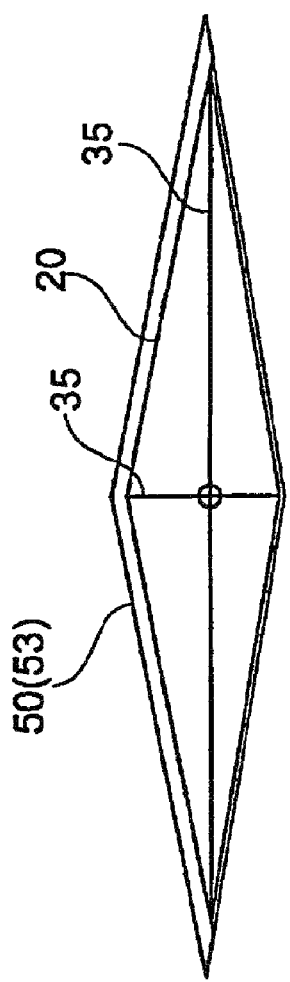

HIGHLY FLEXIBLE ABSORBENT LAMINATE AND METHOD FOR PRODUCTION THEREOF

This application is a national stage application under 35 U.S.C. §371 of International Application No. PCT/DE2011/000338 filed 28 Mar. 2011, which claims priority to German Application No. DE 10 2010 013 288.8 filed 28 Mar. 2010, the disclosures of which are expressly incorporated herein by reference.

BACKGROUND OF THE INVENTION

The invention relates to sheetlike absorbent materials capable of expanding in one coordinate direction at least to create room for the increased volume due to imbibition of liquid to be absorbed.

Absorbent materials are more particularly needed in connection with disposable articles such as, for example, baby diapers, incontinence products and femcare hygiene, or in the sector of absorbent articles for packaging and food technology. This function is traditionally performed by suitable combination products comprising pulp, superabsorbent granules or fibers and liquid-distributing layers comprising synthetic nonwovens, pulp or cotton.

The consumption of raw materials and packaging materials and also the outlay needed for raw materials and for manufacture and sales should be minimized as far as possible both economically and ecologically as well as from the sustainability perspective. As far as the production of hygiene articles is concerned, this means primarily a reduction in primary energy requirements, pulp, transportation volume, packaging films and cardboard and waste volume.

Numerous projects are known in the field of hygiene articles, not only from the literature but also from industrial manufacture, seeking to partially or completely replace the absorbency of cellulose/pulp by using granules of water-absorbing polymers (superabsorbents). It is technically, economically and ecologically desirable for, for example, modern baby diapers or adult incontinence articles to be completely converted to pulp-free absorbent pads in order that the influence of using disposable articles on climate change may be kept as small as possible.

PRIOR ART

Two fundamentally different approaches are being pursued to reduce/eliminate the pulp from baby diapers, incontinence products and femcare hygiene articles. The first approach seeks to replace the pulp by using stretch- or swell-capable thermoplastics as binders between the granules of superabsorbent to retain adherence as the superabsorbent swells up, to join in the swelling movement and to ensure substrate integrity even in the moist state.

The alternative is to incorporate the superabsorbent between two or more carrier layers in discrete sections, in which case the volume enlargement of the superabsorbent due to its swelling due to liquid imbibition takes place alternatively due to elasticity of one or more carrier layers, shirring or stretching of one or more carrier layers during the installation of the superabsorbent in the laminate, or by suitable bonding between the individual carrier layers such that targeted, local rupturing of this bond due to bursting pressure is made possible by the swelling of the superabsorbent without the superabsorbent fully exiting from the carrier layers.

EP 724 418 describes the production of a laminate which consists of two outer plies, of which at least one ply is hydrophilic and which are glued to each other using a water-sensitive pressure-sensitive adhesive, so that isolated unglued sections can punctiformly incorporate superabsorbent which, in the swollen state, specifically breaks open the gluing and achieves the laminate volume increase needed for the swell volume. The disadvantage of this is that only minimal integrity can be achieved for the laminate in the swollen state.

US 20020102392 likewise discloses a method for producing an absorption-capable laminate with incorporated sections of superabsorbents and elastic properties. Here there are sections of superabsorbents, positioned via a vacuum system, between two outer plies, of which one is shirred in the longitudinal direction using a profiled roller and transversely to the manufacturing direction, to obtain a longitudinally extendable laminate, wherein the elasticity and shirring can be increased by using elastic films or nonwovens.

US20020115969 discloses a further method for producing a laminate. Here the longitudinally continuous production of a laminate is described with individual sheetings of superabsorbents which have been installed with hot glue between two outer plies such that there are strips of superabsorbent-covered and superabsorbent-free regions in each case transversely to the manufacturing direction.

The production of a laminate comprising two outer plies with punctiformly incorporated sections of superabsorbents is described in WO 2004071539 and WO 2004071363. A textured vacuum roller is used to cause a first outer layer to develop depressions, which are filled with superabsorbents and fibers and bonded to the second outer layer. Comparable products have long also been used as supports in surgery and patient care.

DESCRIPTION OF THE INVENTION

Superabsorbents undergo a weight increase of 2500-5000% as they imbibe liquid. The associated increase in volume has to be accommodated through suitable flexibility on the part of the surrounding carrier material. This is in principle not a problem in the case of conventional pulp/superabsorbent pads, since the pulp allows expansion in all three dimensions. In the case of so-called superabsorbent laminates, in which superabsorbent granules or superabsorbent/fiber mixtures are fixed using pressure-sensitive adhesive or thermally between two or more plies of nonwovens, film, tissue or the like, this function has to be made possible by the outer plies of the laminate, whether through stretching or through geometric flexibility. But at all times the containment of the superabsorbent has to be ensured without one of the outer plies breaking or the lamination tearing open. It is further desirable that this laminate be elastically extendable not just perpendicularly to its production plane but also within this plane itself in order not only to facilitate the volume enlargement on the part of the superabsorbent due to liquid imbibition but also to combine with other components of the above-identified hygiene articles in not impairing their flexibility and ability to conform to the particular body contour.

The invention accordingly has for its object to provide a laminate which has a high manufacturing capacity and has not only improved area-elastic properties to optimally conform to the body contour of the user but also volume-elastic properties to accommodate large amounts of liquid.

This object is achieved in the present invention by a laminate in that this laminate contains a water-absorbing polymer known as a superabsorbent polymer (SAP) between one or more elastic interplies, wherein the interplies consist of sheetlike lengths of material which are firmly bonded together on the outside surface by individual threads, strands or bands and this laminate is extendable essentially transversely to the production direction and shirred in the relaxed state, and the elastic interplies contain many individual sections or cassettes of superabsorbent and create room for the expansion of the laminate on fluid imbibition perpendicularly to and within the manufacturing plane.

In a further embodiment of the present invention, the appearance of the side-by-side sections/cassettes thus produced corresponds to that of a quilted blanket having an unending number of mutually adjoining sections.

The laminate of the present invention may advantageously be used for modern ultra-thin and elastic hygiene articles, since the laminate is completely elastic and extendable and conforms perfectly to the body contour in both the dry and the moist state.

The laminate of the present invention in one embodiment consists of two outer layers, of which one is hydrophilic and the other is hydrophobic.

The invention further has for its object to provide a production method for the laminate of the present invention enabling the continuous production of absorption-capable laminate with high manufacturing capacity, wherein the end product has not only area-elastic properties to optimally adapt to the body contour of the user but also volume-elastic properties to accommodate large amounts of liquid.

This object is achieved by a method wherein the water-absorbing polymer known as a super-absorbent polymer (SAP) is introduced into one or more elastic interplies, wherein the interplies consist of individual threads, strands or bands between two outer plies of a thusly produced laminate and this laminate is made extendable essentially transversely to the production direction and shirred in the relaxed state, and the elastic interplies therefore contain many individual sections or cassettes of superabsorbent and create room for the expansion of the laminate on fluid imbibition perpendicularly to and within the manufacturing plane.

The present invention's shining and texturing on the skin-sided surface of the laminate, or to be more precise on that side from where the liquid to be imbibed comes into contact with the laminate, is advantageous in ensuring, in association with an appropriate hydrophilic and transportation-capable outer layer, an excellent conductance of liquid not only in the dry but also in the moist state.

Advantageously, a laminate produced in this way is always permeable perpendicularly to its manufacturing plane in the region of the gluing of the elastic plies even in the swollen state without being hindered by the swelling of the superabsorbent, so that the texture of the surface and the choice of appropriate outer layer ensure transportation performance even on the skin-remote side and the skin-sided outer layer can be optimized in respect of back-wetting/skin moisture. It is further the case that laminate integrity is retained.

In a further embodiment, the external layers of the laminate can consist of either a hydrophilic and hydrophobic sheetlike material or both layers can consist of hydrophilic or hydrophobic sheetlike material. Cellulose or pulp can be used as materials for example. The outer sheeting of material can consist of different materials from the group of textile materials, such as cotton, wool, plastics yarns or other plastics-containing compositions or the like, spunbonded webs, paper, self-supporting polymer films of any kind such as polypropylene, polyethylene, nylon or the like, card web, felts or the like.

In the case of the hydrophobic embodiment, the sheetlike hydrophobic material is microapertured beforehand. Advantageously microaperturing was found to create "channeling" which results in faster removal of liquid and a distinct reduction in skin moisture. In a further embodiment, channeling is effected via a chemical reaction with the pressure-sensitive adhesive which is applied to the sheetings of material.

According to the invention, first the front end of the first outer textile sheeting of material is applied to the end portion of an elongate rod- or tube-shaped core and, by imposing an advancement movement around the core, folded into a shape which is closed in a hoselike form.

In the course of the processing method, the advancement movement on the core serves, through tapering of the cross section of the core, to shorten the circumference of this hose to the effect that excess material is ducted through ducting rails or rods outside the hose into suitable cutouts in the core. Subsequently, one or more than one, preferably two and more preferably more than two driven feed devices 11 and 14 which ring the mold and are contrarotatory in pairs loosely withdraw groups of elastic threads or strands 50 and 53 from circumferentially spaced-apart individual guides 17 and place them with friction-caused low pre-tensioning around the first outer sheeting of material in the course of the advancement on the core. Areal pattern 32 of elastic threads or strands which surrounds the tube of the first outer sheeting of material in a cruciformly symmetrical manner has a pressure-sensitive adhesive 29 applied to it in thread form, which wets and enfolds the essentially bare elastic threads. In the continued course of the forward feed movement, the cross section of the core is enlarged to tauten the hose of the first outer sheeting of material and thereby cause it to come into contact with the elastic threads and finally be brought into a flat shape. On both sides of this flat hose, a pair of advancement or contact rollers 38 is used to bond two individual sheets of the second outer material layer 32 onto the free surface of the first outer material sheeting 20 and the elastic threads 17 provided with the pressure-sensitive adhesive 29. As this bond is being formed, individual tracks of superabsorbent 47 are introduced on both sides of the hose of the first outer sheeting of material, between it and the supplied second outer sheeting of material. Finally, the hose thus produced is severed lengthwise into individual sheetings and these are traversingly wound onto individual rolls or deposited in boxes.

The folding-in of the hose of the first sheeting of material and producing the circumferential elasticity of the hose by spreading apart the first outer sheeting of material by expanding the elastic thread pattern 32 are advantageous over comparable prior art winding processes for elastic hoses based on pre-tensioned threads or bands as for example from WO 03041627 or DE 102004026070 in producing an appreciable reduction in complexity by eliminating the drive for individual guides of the threads and increased productivity in proportion with the transverse extensibility of the laminate. This is based on the limiting speed which limits the manufacturing speed of the ring-shaped feed devices. The invention is further advantageous in reducing the width of the applicator system for the pressure-sensitive adhesive 29 to the same degree.

Since, following application of the elastic threads or bands to the hose of the first outer sheeting of material, this hose is only touched punctiformly and is otherwise bare, a pressure-sensitive adhesive applied spirally or meanderingly is forced through the areal pattern of the elastic threads. This is preferable in order that these elastic threads or bands may be enfolded and be oriented essentially around the threads after spreading apart of the hose or the first outer sheeting of material. This produces a glue pattern which corresponds to the areal pattern 32 and which is as shown in FIG. 4 for example, and which owing to the enfolding of the elastic threads bonds these adheringly not only to the first but also to the second outer sheeting of material in the further course of the advancement movement on the core.

The outer sheeting of material can consist of different materials from the group of textile materials, such as cotton, wool, plastics yarns or other plastics-containing compositions or the like, spunbonded webs, paper, self-supporting polymer films of any kind such as polypropylene, polyethylene, nylon or the like, card web, felts or the like.

In a further embodiment, the core 5, as shown in FIG. 2a for example, consists of guiding struts 35 which guide the material sheeting 20. Arranged therein between are storage struts 38 (FIG. 2a) into which excess material of the hose of material sheeting 20 is forced during the tapering of the core through corresponding guiding rails 8 (FIG. 2b).

Advantageously, the first outer sheeting of material, once it has been pressed into the storage struts, can easily be maintained by negative pressure in a position closely bearing against the guiding and storage struts of the core, and be pulled with low friction over the core. Further alternatives for fixing include the introduction of compressed air or electrostatic charging, which likewise lead to the closely bearing position and are held and pulled with low friction over the core.

Spreading the core apart after the elastic interlayers and the pressure-sensitive adhesive have been applied is advantageously achieved when guiding struts, which are mutually opposite pairwise, gradually widen in the further course of the core in their expansion direction transversely to the longitudinal axis of the core and a further pair of guiding struts is decreased in its width to the same degree, so that the hose of the first outer layer is continuously pulled out of the storage struts and pulled taut over the tips of the guiding struts and is thus brought into sheetlike contact with the pressure-sensitively glued elastic plies (FIG. 2c), lastly brought into a flat state, in the continued course of the advancement movement by further synchronous pairwise widening or, respectively, width reduction of the guiding struts while maintaining essentially the same length of circumference (FIG. 2d).

Advantageously, the core 5 is disposed to be perpendicular in its longitudinal direction such that the advancement rolls 56 are situated at the lower end of core 5 (FIG. 1).

The water-absorbing polymer (superabsorbent) is supplied according to the invention in separate volumetrically or weight-dosed continuous individual lines or tracks. The water-absorbing polymer (superabsorbent) can either be introduced into the glue-free regions of the areal pattern in an intermittent manner by pulsating compressed air or pistons, or be intermittently deflected in line with the areal pattern in a direction transversely to the centrifugal direction of the hose of the first outer sheeting of material. For simplicity of use, it can be sufficient to allow these individual tracks to trickle down continuously, in which case it is advantageous to supply two individual tracks per cassette of the areal pattern.

According to the invention, the advancement rollers can be sectionally provided with negative-pressure regions, so that the water-absorbing polymer (superabsorbent) becomes laid down on the glue-free section/cassettes of the areal pattern in a precise manner, so that no water-absorbing polymer (superabsorbent) escapes into the adjacent region.

In a further embodiment, the hose of the first outer material sheeting 20 can be relaxed in the transverse direction by reducing the width of the guiding struts before being supplied into the advancement rolls 56, so that it has a slight degree of waviness at the time the second outer sheeting 44 is supplied. This favors the formation of pockets in the region of the nonglued zones of areal pattern 26, which facilitate the laydown of superabsorbent 33.

In a further embodiment of the invention, this waviness can be policed to advantageously control the ratio of the widths of the first and second outer sheetings of material relative to each other such that the laminate produced has a higher degree of waviness on the side of the first outer layer than on the side of the second outer layer. This makes it possible to minimize the particular costly material of the outer layers 20 and 44 while keeping the swell volume of individual cassettes the same.

DESCRIPTION OF THE DRAWINGS

The drawings which follow are intended to more particularly illuminate the present invention without restricting it to these embodiments.

In the drawings

FIG. 2c shows the construction of the core in the region of the spreading apart of the core;

FIG. 2d shows the construction of the core after spreading apart is complete;

Said FIG. 1 shows, depicted in a simplified and highly schematicized manner, the device 2 for producing the laminate. The device consists in this embodiment of an elongate core 5 having a square cross section, which is surrounded by two feed means 11 and 14 which are spaced apart from each other in the longitudinal direction. These feed means are rotationally driven in opposite directions illustrated by the arrows a and b. Individual guides 17 for elastic threads, bands or strands are spaced apart from each other on these ring-shaped feed means in the circumferential direction in each case. The elastic elements are withdrawn from their wound package in the axial direction through these individual devices, leading them in the direction of core 5.

Said FIG. 2*a* shows a rotatably mounted and driven material roller 26, from which a first outer material sheeting 20 is conveyed in the present embodiment under sheeting tension control and folded via a forming shoulder 6 into a hose of rectangular cross section and laid onto the front end of core 5 formed by multiple struts 35, 38. Advantageously, the overlap of the first outer material sheeting 20 is fixed as a result in the course of forming the hose by applying a pressure-sensitive adhesive, welding or mechanical arrest.

In FIG. 2*b*, the hose thus formed is subsequently guided over the cross-sectionally tapered core, so that the hose merely guides the core on the ends of the guiding struts 35, which shorten in their width, and inbetween material of the hose is guided using guiding rails or wires 8 in vacant spaces formed by storage struts 38 disposed between the guiding struts.

In FIG. 3, this hose, thus shortened in its circumference, is subsequently guided by two contrarotatingly turning feed means 11 and 14. In the feed means, individual elastic threads, bands or strands 50, 53 are each withdrawn by circumferentially spaced-apart individual guides 17 of stationary packages or rolls and laid down onto the hose of the first outer material layer 20. The superposition of the rotary motions of the two feed means 11, 14 by the advancement of the first material layer 20 results in an oppositely diagonal pattern of the elastic elements 50, 53, which only contacts the first layer material layer on the tips of the guiding rails 35 of core 5, but is otherwise bare, FIG. 3.

Figure 4:
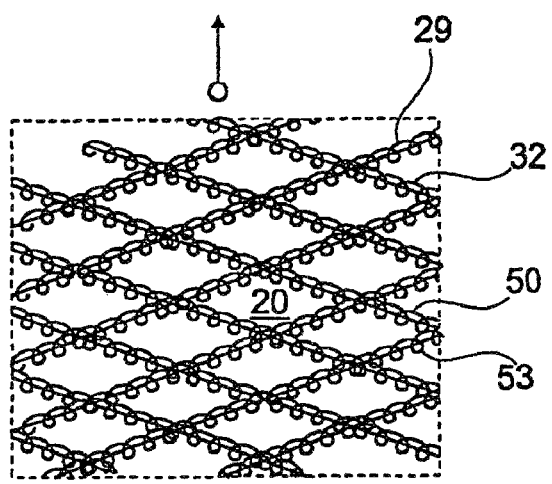
FIG. 4 shows areal patterns, obtained on using two oppositely driven feed means as per FIG. 3, of elastic threads or strands and of applied pressure-sensitive adhesive in a laminate produced in the manner of the invention.

In the continued course of advancement on the core 5, the elastic threads 50 and 53 have pressure-sensitive adhesive applied to them, preferably as a curtain of spiraling or meandering threads, which on impingement on the bare oppositely diagonal pattern of elastic threads 50 and 53 is diverted by these and preferentially wets and enfolds the elastic threads, but specifically cross-over points between threads 50 and 53, FIG. 4.

In the continued course of advancement on the core 5, the latter is spread in its cross section such that any two opposite guiding struts are expanded in their width, and a complementary pair of guiding struts is reduced in its width, to the effect that initially the material of the first layer 20 remaining in the storage struts 38 of the core 5 is continuously detached and the hose of the first material layer 20 is tensioned taut over the ends of the guiding rails 35 (FIG. 2*c*). This brings the hose of the first material sheeting 20 into sheetlike contact with the pattern of elastic elements 17 and of the pressure-sensitive adhesive applied thereto. The process of pairwise widening of the guiding struts 35 and the attendant diminution of complementary guiding struts is continued in the course of the continued advancement of the hose of the first material sheeting 20 over the core 5 to the effect that ultimately the hose of the first material sheeting 20 is only guided over the ends of two guiding struts 35 of core 5 and hence is virtually planar.

In a further step, this hose thus formed into a flat shape is introduced into a device of two driven opposite advancement elements, in the form of two rolls or rollers 56 in the present embodiment, which supply the advancement for unrolling the first outer layer 20 of the material roll 26 and the transportation of all materials over the core.

The advancement rollers 56 provide withdrawal and feeding, preferably under sheeting tension control, of an individual sheeting each of the second outer layer 44 of two mutually spaced-apart, rotatingly driven material rolls 41, on both sides of the material sheeting 20, and sheetlike bonding thereof to the first material layer 20 and the elastic areal pattern 32 via the pressure-sensitive adhesive 29.

Figure 5:
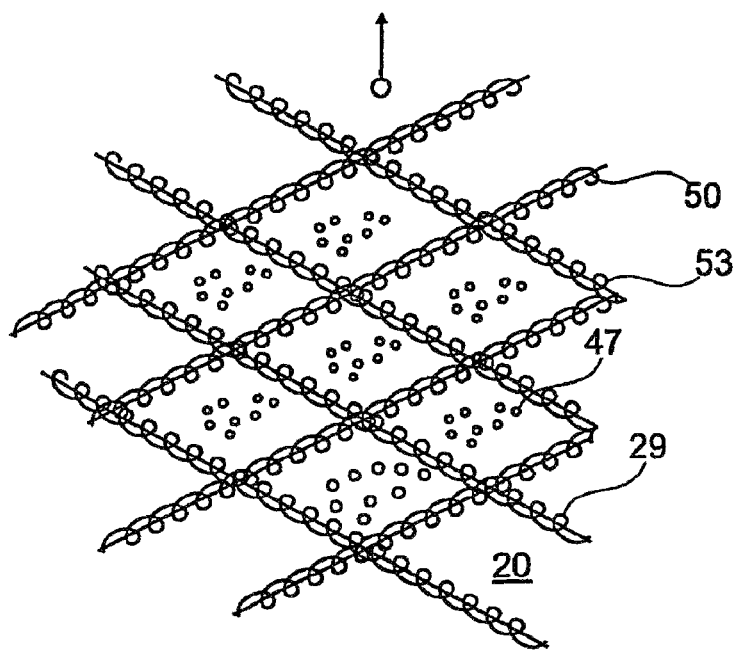
FIG. 5 shows areal patterns, obtained on using two oppositely driven feed means as per FIG. 3, of elastic threads or strands and of punctiformly supplied pulverulent filler material in the laminate produced in the manner of the invention.
Figure 5B:
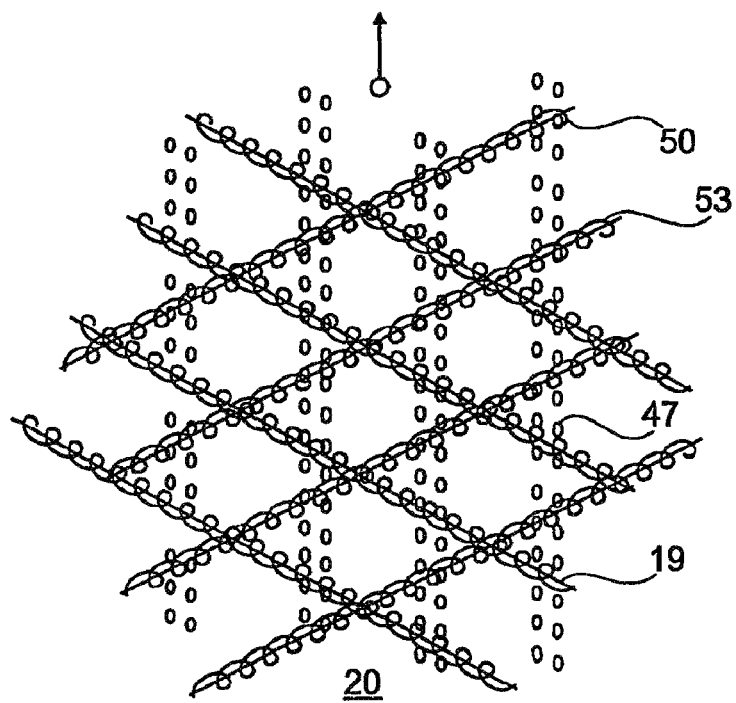
FIG. 5b shows areal patterns, obtained on using two oppositely driven feed means as per FIG. 3, as elastic threads or strands and of pulverulent filler material supplied continuously in discrete individual lines in a laminate produced in the manner of the invention.
Figure 5C:
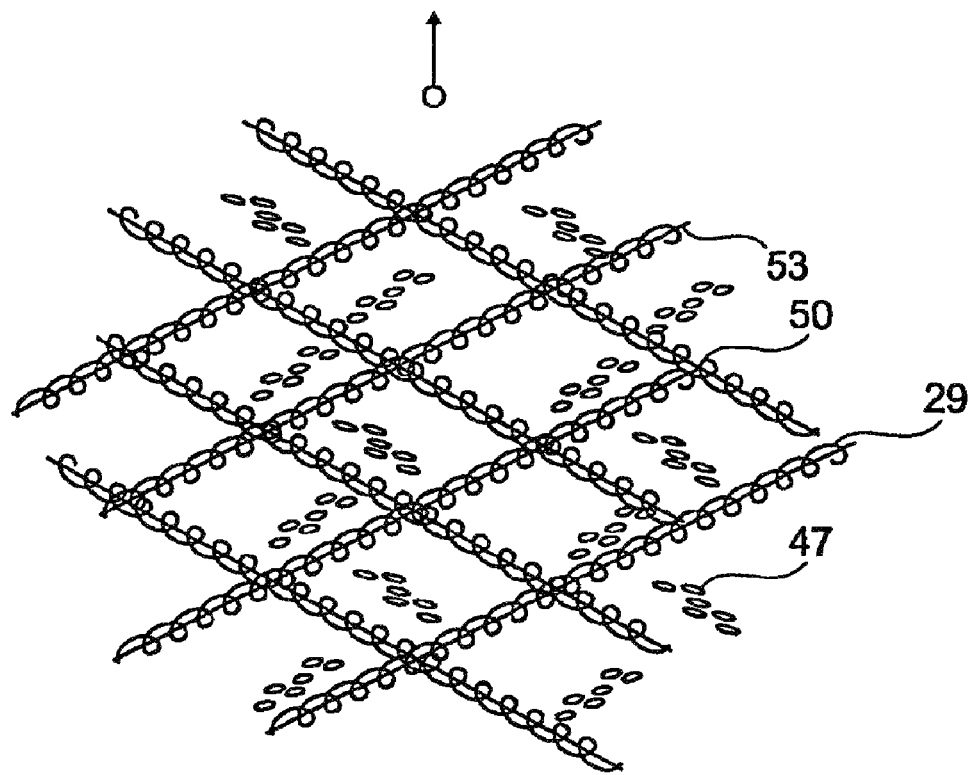
FIG. 5c shows areal patterns, obtained on using two oppositely driven feed means as per FIG. 3, as elastic threads or strands and of pulverulent filler material supplied continuously in discrete individual lines, intermittently deflected transversely to the production direction in a laminate produced in the manner of the invention.

As the flattened hose of the first material sheeting 20 is brought together with the supplied planar lengths of the second material sheeting 44 by the advancement unit 56, a water-absorbing polymer (superabsorbent 47) is introduced on both sides of the hose in a perpendicular manner such that, in line with the areal pattern 32, individual lines or tracks adapted individually volumetrically or grammetrically to the advancement speed of the hose of the first material sheeting 20 are continuously trickled in, resulting in a product pattern as per FIG. 5*b*. In an alternative version, not depicted here, these tracks can also be mechanically or pneumatically deflected transversely to the flow direction in accordance with areal pattern 32 in an intermittent or oscillating manner (product pattern as per FIG. 5*c*) or these tracks can be deflected either by pulsating or intermittent compressed air, mechanical pistons or mechanical deflection of the conveying means transversely to the flow direction of the hose of the first material sheeting 20 onto the centers of the regions of this hose which are free of pressure-sensitive adhesive and formed by the areal pattern 32, for example in accordance with the product pattern of FIG. 5. In a further version not depicted here, the targeted application of water-absorbing polymer (superabsorbent 47) is effected by the advancement rolls which are sectionally provided with negative-pressure regions, so that the laydown of water-absorbent polymer (superabsorbent) on the glue-free section/cassettes of the areal pattern is effected in a precise manner, so that no water-absorbing polymer (superabsorbent) escapes into the adjoining area.

In one embodiment, the pressure-sensitive adhesive is set by the contact pressure of the advancement rolls 56 after bonding the two outer layers 20 and 44 to each other, wherein the incorporation of the water-absorbing polymer (superabsorbent 47) takes place between the incorporated elastic elements 50, 53, and this multi-ply hose thus formed is severed longitudinally into individual sheetings in the course of the continued advancement movement. These sheetings can selectively be transversingly wound up on rolls movement or deposited in boxes or coiled up.

Figure 6:
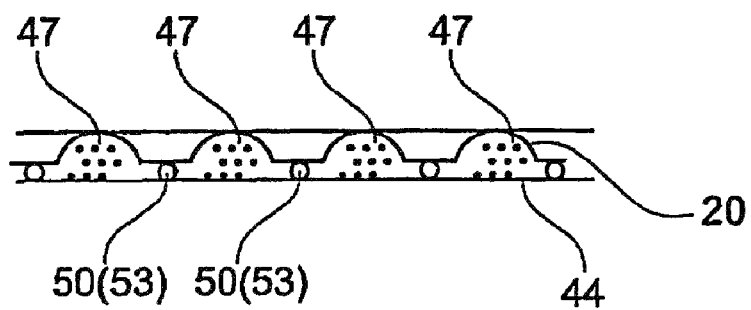
FIG. 6 shows a schematic depiction of the laminate produced according to the invention on unweighting the hose of the first sheeting of material and the incorporated elastic interplies transversely to the manufacturing direction thereof before introducing the superabsorbent and bonding to the second outer sheeting of material.

FIG. 6 depicts a further embodiment. Here the width of the flat hose comprising a first material sheeting 20 and the areal pattern of elastic elements 32, having been spread apart into the flat state as in FIG. 2*d*, is relaxed and shirred by reducing the width of the guiding rails 35 such that bonding to the otherwise essentially flat second outer material sheeting 44 produces an elastic, absorption-capable laminate. This laminate has by virtue of the outside surface formed by the first outer sheeting of material a higher degree of shining than the side formed by the second outer layer.

Figure 7A:
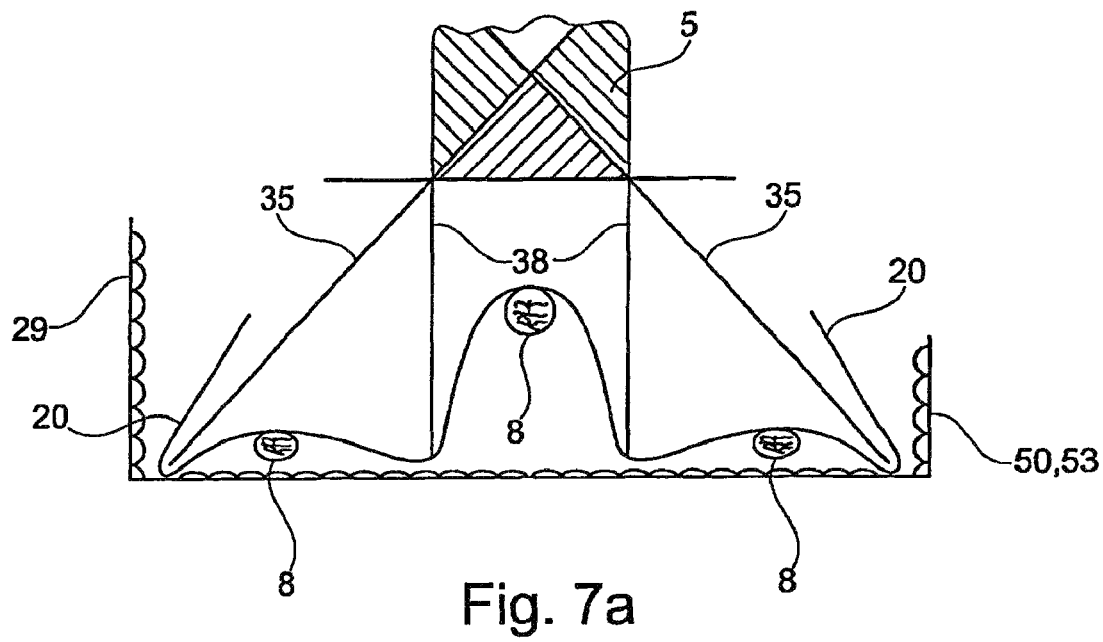
FIG. 7a shows a schematic depiction of a detail from the cross section of the core on using two storage struts between respectively two guiding struts and policing the sectionwise intake of the first outer layer by positioning the guiding rails.
Figure 7B:
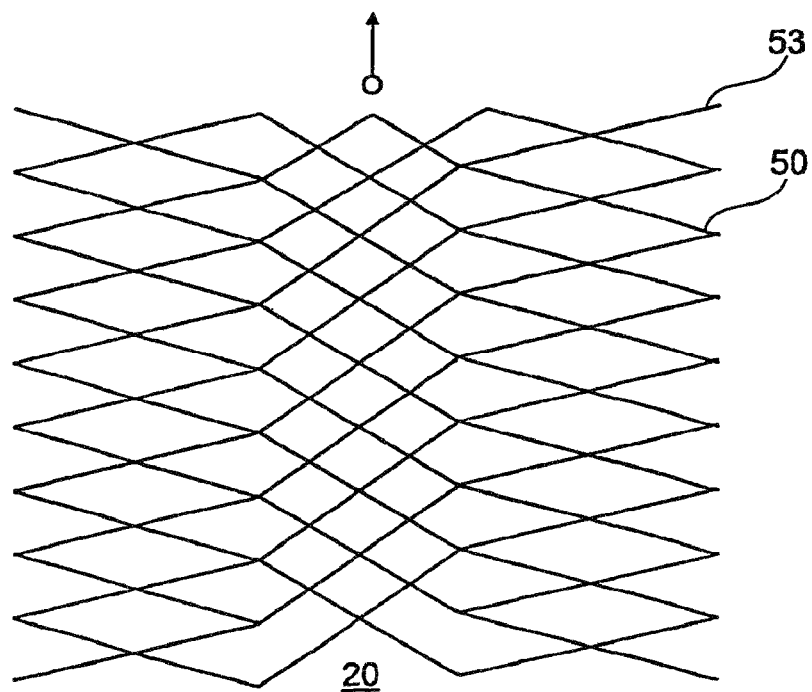
FIG. 7b shows areal patterns of elastic threads of the elastic laminate produced according to FIG. 7a, in the planar, relaxed state.

In a further embodiment, the planar laminate can be endowed transversely to its production direction with sections/cassettes of differing shining for the external plies and thus differing swell volume, leading by controlling the superabsorbent distribution transversely to the production direction of the laminate to an advantageous transverse distribution of absorbency. FIG. 7*a* shows two storage struts 38 per guiding strut pair 35, which are inserted by disposing the guiding rails 8 in the formed-out storage sections of core 5 in the transverse direction to the advancement direction of differing sheeting widths of excess first outer sheeting material 20 due to the tapering of the core 5. In the continued course of the advancement movement and spreading apart of the core 5, initially the spreading of the storage struts 38 serves to contact, on the tips thereof, the material sheeting 20 with the pressure-sensitive adhesive 29 of the elastic plies 50, 53 and then the spreading apart of core 5 is continued within the meaning of FIGS. 2b-d and the combination with the superabsorbent and the second outer material sheeting 44 is completed to ultimately form a longitudinally severed laminate which in the relaxed, planar state has a strutwise variation in the transverse direction of the shining of the external layers and hence ultimately of absorbency, FIG. 7b.

It can be advantageous to achieve the function of pressing the first outer material sheeting into the vacant spaces of the storage struts instead of the guiding rails 8 by negative-pressure from the guiding core, by static charge build-up on the first outer material sheeting 20 versus the struts 35, 38 of the core, or by applying compressed air to the outside surface of the hose.

Figure 1:
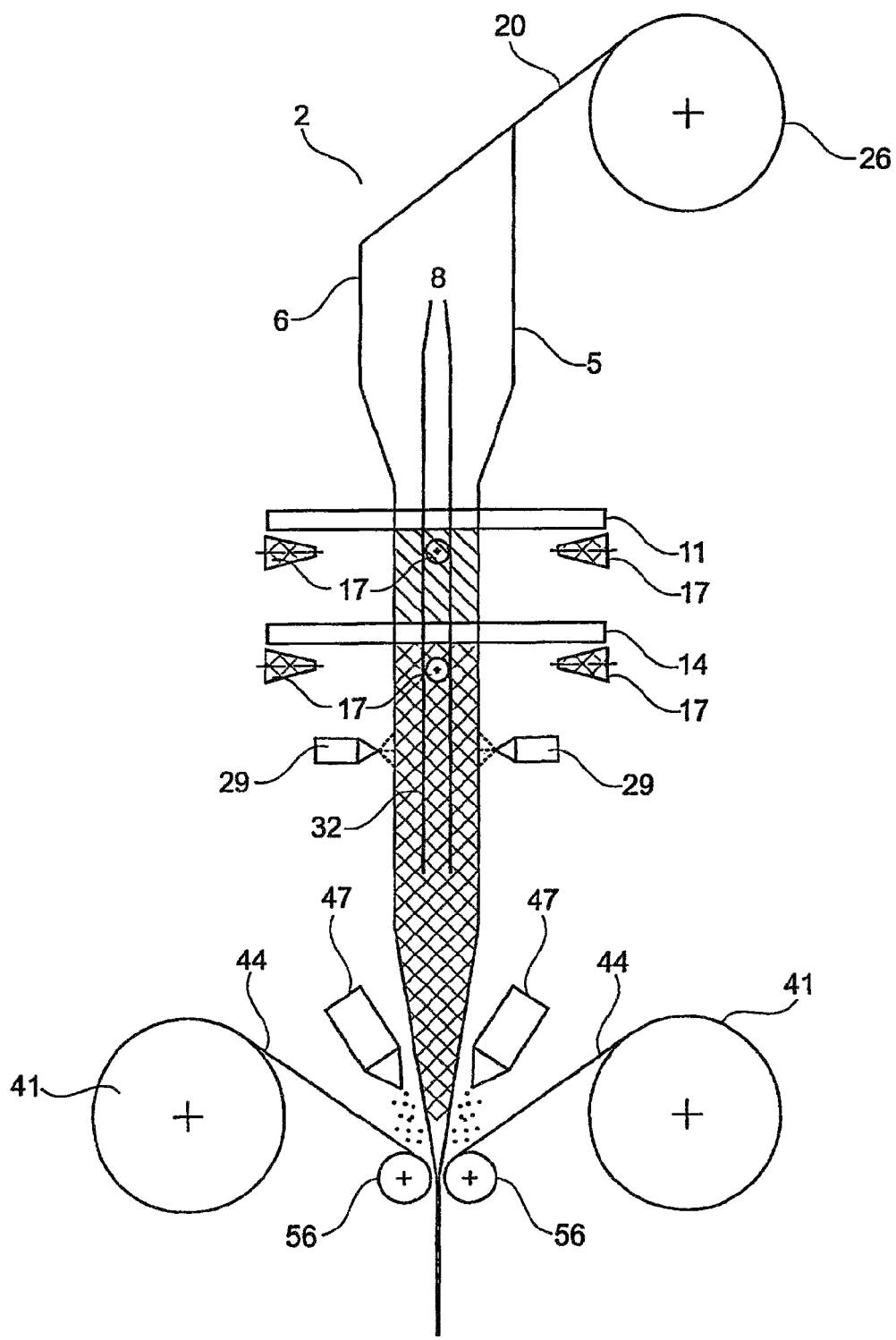
FIG. 1 shows a highly schematicized depiction of the side view of the essential functional elements of an embodiment of the inventive method.
Figure 2A:
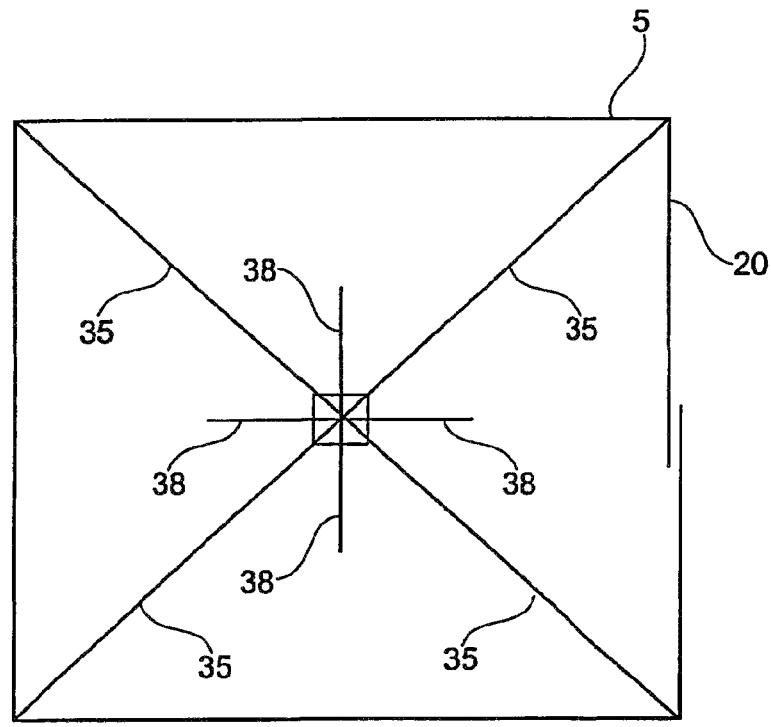
FIG. 2a shows the construction of the core comprising guiding and storage struts.
Figure 2B:
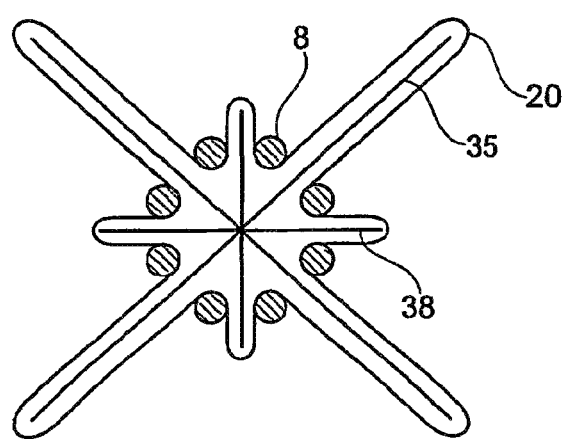
FIG. 2b shows the construction of the core comprising guiding and storage struts and guiding rails in the region of the tapering of the core.
Figure 3:
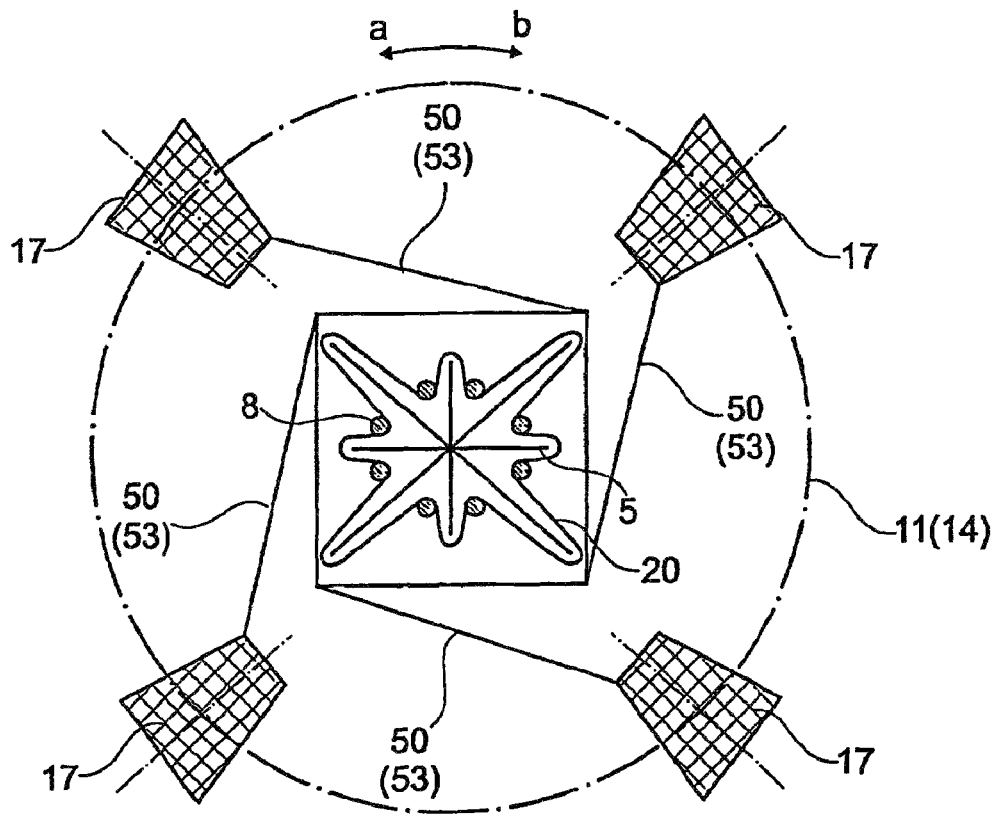
FIG. 3 shows the arrangement of individual guides in one of the feed means provided in the device as per FIGS. 1 and 2 for applying groups of untensioned or lightly tensioned threads or strands.

It can further be sensible and advantageous to achieve the functions of the respectively four guiding and storage struts from FIGS. 2a and 2b by means of a correspondingly higher number of struts in order that specifically in the case of large sheeting widths for the first outer sheeting material 20 or high storage requirements a good conductance of material may be achieved on tapering the cores 5.

Even if the isolation of individual sections of superabsorbents in glue-free regions of an otherwise mutually glued-together sheeting material comprising two outer material sheetings 20 and 44 and incorporating elastic plies 50 and 53 is advantageous for the swelling effect and volume enlargement on the part of superabsorbent 47 in the liquid imbibition in accordance with the intended use, it can be sensible to wet the second outer material sheeting 44 with an additional slight layer of pressure-sensitive adhesive before combining with the first outer material sheeting 20 in a sheetlike manner or in longitudinal strips in order that the superabsorbent may be fixed as sheetlike as possible to thereby preempt any possible clumping of this material before commencement of liquid imbibition and to improve the haptics of the laminate thus produced.

DESIGNATIONS OF ELEMENTS IN DRAWINGS

2 Overall device
55 Core
6 Forming shoulder of first outer material sheeting
8 Guides of first outer material sheeting
11 First guide means
14 Second guide means
1017 Individual guide of elastic threads
20 First layer of outer material sheeting
23 Forming shoulder
26 Material roller of first outer material sheeting
29 Pressure-sensitive adhesive
1532 Areal pattern of elastic threads
35 Guiding struts of core
38 Storage struts of core
41 Material roller of second outer material sheeting
44 Second outer material sheeting
2047 Water-absorbing polymer (superabsorbent)
50 Individual thread of first elastic interply
53 Individual thread of second elastic interply
56 Tensile rollers

The invention claimed is:

1. A highly flexible, absorbent laminate comprising a first layer of a hydrophilic and transportation capable outer material sheeting for conductance of liquid; a second layer outer material sheeting; a plurality of interplies interposed between said first layer of a hydrophilic and transportation capable outer material sheeting and second layer of outer material sheeting wherein said plurality of interplies comprise intersecting elastic threads arranged in an areal pattern; and wherein the intersection of the first layer of a hydrophilic and transportation capable outer material sheeting, the second layer of outer material sheeting, and said plurality of interplies define a plurality of individual cassettes; an adhesive to bond the plurality of interplies to the first layer of a hydrophilic and transportation capable outer material sheeting and second layer of outer material sheeting in said areal pattern; and a superabsorbent polymer located between the first layer of a hydrophilic and transportation capable outer material sheeting and a second layer of outer material sheeting, wherein the superabsorbent polymer is contained in the plurality of individual cassettes, and wherein said laminate is elastically extendable transversely to a production direction and shined in a relaxed state creating room for the expansion of the plurality of individual cassettes in the perpendicular direction to the manufacturing plane and within the manufacturing plane, and wherein the expansion of the laminate and the plurality of individual cassettes results from the fluid imbition of the superabsorbent polymer and wherein the laminate is liquid permeable and transportation capable perpendicularly to the manufacturing plane in the region of the adhesive which bonds the plurality of interplies to the first layer of a hydrophilic and transportation capable outer material sheeting and second layer of outer material sheeting in said areal pattern.

2. The laminate as set forth in claim 1, characterized in that the second layer outer material sheeting comprises microapertured hydrophobic material.

3. A method for producing a highly flexible, absorbent laminate comprising a first layer of a hydrophilic and transportation capable outer material sheeting for conductance of liquid; a second layer of outer material sheeting where between are incorporated a plurality of pre-tensioned interplies comprising intersecting elastic threads arranged in an areal pattern, and superabsorbent polymer granulate, the laminate produced by the first layer of hydrophilic and transportation capable outer material sheeting being folded over an elongate core to form a tube, this tube being reduced in size by tapering the cross section of the core and being wrapped with groups of substantially untensioned elastic threads in a contrarotating manner in the form of a tube reinforcement, pressure-sensitive adhesive being applied to the elastic threads and these elements being brought into contact with the tube of the first layer of hydrophilic and transportation capable material sheeting by spreading over the core under tension, both together being brought into a flat shape in the further course of the forward feed movement of the tube on the core, and by intermittent or continuous supply of individual tracks of superabsorbent polymer granulate being bonded to two lengths of a second layer of outer material sheeting and being longitudinally cut open to form elastic individual lengths, wherein said adhesive bonds the plurality interplies to the first layer of a hydrophilic and transportation capable outer material sheeting and second layer of outer material sheeting in said areal pattern, and wherein the intersection of the first layer of a hydrophilic and transportation capable outer material sheeting, the second layer of outer material sheeting, and said plurality of interplies define a plurality of individual cassettes, and wherein the superabsorbent polymer is contained in the plurality of individual cassettes, and wherein said laminate is elastically extendable transversely to a production direction and shined in a relaxed state, and wherein the expansion of the laminate and the plurality of individual cassettes results from the fluid imbition of the superabsorbent polymer granulate, and wherein the laminate is liquid permeable and transportation capable perpendicularly to the manufacturing plane in the region of said pressure-sensitive adhesive which bonds the plurality of interplies to the first layer of a hydrophilic and transportation capable outer material sheeting and second layer of outer material sheeting in said areal pattern.

4. The method as claimed in claim 3, characterized in that one of the first and second layers of outer material sheeting is a self-supporting film.

5. The method as claimed in claim 3, characterized in that said self-supporting film is water vapor permeable.

6. The method as claimed in claim 3, characterized in that the second layer of outer material sheeting is water impermeable, being rendered permeable in combination with the pressure-sensitive adhesive.

7. The method as claimed in claim 3, characterized in that the second layer of outer material sheeting is water impermeable, being rendered punctiformly permeable by mechanical pressure or aperturing while the two outer layers are being bonded together.

8. The method as claimed in claim 3, characterized in that the first layer of outer material sheeting is relaxed and shortened in its transverse direction before the bonding to the second outer layer by exploiting the pre-tensioning of the applied interplies such that, in combination with the second layer of outer material sheeting, the shirring in a relaxed state is formed by the first layer of outer material sheeting.

9. A highly flexible absorbent laminate produced by the method as claimed in claim 3.

* * * * *

UNITED STATES PATENT AND TRADEMARK OFFICE
CERTIFICATE OF CORRECTION

PATENT NO. : 9,056,033 B2  
APPLICATION NO. : 13/636471  
DATED : June 16, 2015  
INVENTOR(S) : Wilfried Fenske Page 1 of 1

It is certified that error appears in the above-identified patent and that said Letters Patent is hereby corrected as shown below:

In the claims

Column 10,

Line 23, "and shined in" should read -- and shirred in --.

Column 11,

Line 4, "and shined in" should read -- and shirred in --.

Column 12,

Lines 1-18, should be replaced with the following:

-- 5. The method as claimed in claim 4, characterized in that said self-supporting film is water vapor permeable.

6. The method as claimed in claim 3, characterized in that the first layer of outer material sheeting is relaxed and shortened in its transverse direction before the bonding to the second outer layer by exploiting the pre-tensioning of the applied interplies such that, in combination with the second outer length of material, the resulting exhibits shirring in a relaxed state on the sheeting side formed by the first layer of outer material sheeting.

7. The method as claimed in claim 3, characterized in that the superabsorbent polymer granulate-facing side of the second layer of outer material sheeting has an additional pressure-sensitive applied to it in the dry state for bonding the tracks of superabsorbent polymer granulate.

8. A highly flexible and absorbent laminate produced as claimed in claim 3.

9. A highly flexible absorbent laminate produced as claimed in claim 3. --.

Signed and Sealed this  
Sixth Day of October, 2015

Michelle K. Lee  
*Director of the United States Patent and Trademark Office*